US 6,632,020 B2

(12) United States Patent
Kaufhold et al.

(10) Patent No.: US 6,632,020 B2
(45) Date of Patent: Oct. 14, 2003

(54) METHOD AND APPARATUS FOR CALIBRATING AN IMAGING SYSTEM

(75) Inventors: John Patrick Kaufhold, Altamont, NY (US); John Eric Tkaczyk, Delanson, NY (US); Dinko E. Gonzalez Trotter, Clifton Park, NY (US); Jeffrey Wayne Eberhard, Albany, NY (US); Jerry A. Thomas, Potomac, MA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/975,892

(22) Filed: Oct. 12, 2001

(65) Prior Publication Data

US 2003/0072417 A1 Apr. 17, 2003

(51) Int. Cl.[7] .............................................. G01D 18/00
(52) U.S. Cl. .......................................... 378/207; 378/51
(58) Field of Search ........................ 378/207, 62, 98.8, 378/51, 53, 56; 250/252.1

(56) References Cited

U.S. PATENT DOCUMENTS

| 5,565,678 | A | | 10/1996 | Manian |
| 5,719,916 | A | | 2/1998 | Nelson et al. |
| 5,805,665 | A | | 9/1998 | Nelson et al. |
| 5,821,541 | A | | 10/1998 | Tumer |
| 5,844,965 | A | | 12/1998 | Galkin |
| 5,881,127 | A | | 3/1999 | Molloi et al. |
| 5,917,877 | A | * | 6/1999 | Chiabrera et al. .......... 378/207 |
| 6,059,727 | A | | 5/2000 | Fowlkes et al. |
| 6,104,777 | A | | 8/2000 | Darboux et al. |
| 6,302,582 | B1 | * | 10/2001 | Nord et al. ................. 378/207 |
| 6,315,447 | B1 | * | 11/2001 | Nord et al. ................. 378/207 |

* cited by examiner

Primary Examiner—Drew A. Dunn
Assistant Examiner—Courtney Thomas
(74) Attorney, Agent, or Firm—Armstrong Teasdale LLP

(57) ABSTRACT

A method for calibration of an imaging system includes providing a calibration phantom system including a first phantom element material block having a first surface at a first height, wherein the first phantom element material block at least partially includes a first material having a first attenuation coefficient. Providing a calibration phantom system also includes providing a second phantom element material block having a second surface at a second height different than the first height, the second phantom element material block at least partially including a second material having a second attenuation coefficient different than the first attenuation coefficient, wherein the first phantom element material block and said second phantom element material block are co-positioned on a detector. The method also includes imaging the calibration phantom system to obtain phantom images, processing the phantom images, and extracting a plurality of calibration values from the processed phantom images.

23 Claims, 6 Drawing Sheets

METHOD AND APPARATUS FOR CALIBRATING AN IMAGING SYSTEM

STATEMENT REGARDING FEDERALLY SPONSORED RESEARCH & DEVELOPMENT

The government may have rights in this invention pursuant to government contract 22287 under MDA 905-00-1-0041.

BACKGROUND OF THE INVENTION

This invention relates generally to an imaging system, and more particularly, to calibration of a medical imaging system.

In at least some known imaging systems, a radiation source projects a cone-shaped beam which passes through the object being imaged, such as a patient and impinges upon a rectangular array of radiation detectors. In some known tomosynthesis systems, the radiation source rotates with a gantry around a pivot point, and views of the object are acquired for different projection angles. As used herein "view" refers to a single projection image or, more particularly, "view" refers to a single projection radiograph which forms a projection image. Also, as used herein, a single reconstructed (cross-sectional) image, representative of the structures within the imaged object at a fixed height above the detector, is referred to as a "slice". And a collection (or plurality) of views is referred to as a "projection dataset." A collection of (or a plurality of) slices for all heights is referred to as a "three-dimensional dataset representative of the image object.

One known method of reconstructing a three-dimensional dataset representative of the imaged object is known in the art as simple backprojection, or shift-and-add. Simple backprojection backprojects each view across the imaged volume, and averages the backprojected views. A "slice" of the reconstructed dataset includes the average of the backprojected images for some considered height above the detector. Each slice is representative of the structures of the imaged object at the considered height, and the collection of these slices for different heights, constitutes a three-dimensional dataset representative of the imaged object. Alternatively, in a two-dimensional scan, such as, for example, a Cranio-caudal scan (CC scan) or a mediolateral-oblique scan (MLO), only a single slice is acquired constituting a two-dimensional dataset representative of the imaged object.

Uniformity between individual detector elements is important for securing good image quality of mammography images. Otherwise, anomalies may occur in the collected data. A consequence of data anomalies is image distortions, commonly referred to as artifacts. Detector uniformity may be impacted by many factors which include, but are not limited to, radiation damage, moisture damage, electromagnetic fields, and sensitivity of the scintillator materials. To correct for this uniformity, periodic calibrations of the detector are required.

In at least one known method of calibration, a reference set of measurements of known glandular and fatty tissue composition is required. Collecting this set of reference measurements may require multiple scans of the object being imaged.

BRIEF DESCRIPTION OF THE INVENTION

A calibration phantom system for use with an imaging system is provided. The calibration phantom system includes a first phantom element material block having a first surface at a first height, wherein the first phantom element material block at least partially includes a first material having a first attenuation coefficient. The calibration phantom system also includes a second phantom element material block having a second surface at a second height different than the first height, the second phantom element material block at least partially includes a second material having a second attenuation coefficient different than the first attenuation coefficient, wherein the first phantom element material block and the second phantom element material block are co-positioned on a detector.

A method for calibration of an imaging system including a radiation source and a digital detector is provided. The method includes providing a calibration phantom system including a first phantom element material block having a first surface at a first height, wherein the first phantom element material block at least partially includes a first material having a first attenuation coefficient. Providing a calibration phantom system also includes providing a second phantom element material block having a second surface at a second height different than the first height, the second phantom element material block at least partially including a second material having a second attenuation coefficient different than the first attenuation coefficient, wherein the first phantom element material block and the second phantom element material block are co-positioned on a detector. The method also includes imaging the calibration phantom system to obtain phantom images, processing the phantom images, and extracting a plurality of calibration values from the processed phantom images.

A computer readable medium encoded with a program executable by a computer for calibration of an imaging system including a radiation source and a digital detector is provided. The program is configured to instruct the computer to image the calibration phantom system, wherein the calibration phantom system includes a first phantom element material block having a first surface at a first height, wherein the first phantom element material block at least partially includes a first material having a first attenuation coefficient. The calibration phantom system also includes a second phantom element material block having a second surface at a second height different than the first height, the second phantom element material block at least partially including a second material having a second attenuation coefficient different than the first attenuation coefficient, wherein the first phantom element material block and the second phantom element material block are co-positioned on the detector. The program is also configured to instruct the computer to obtain phantom images, process the phantom images, and extract a plurality of calibration values from the processed phantom images.

DETAILED DESCRIPTION OF THE INVENTION

Figure 1:
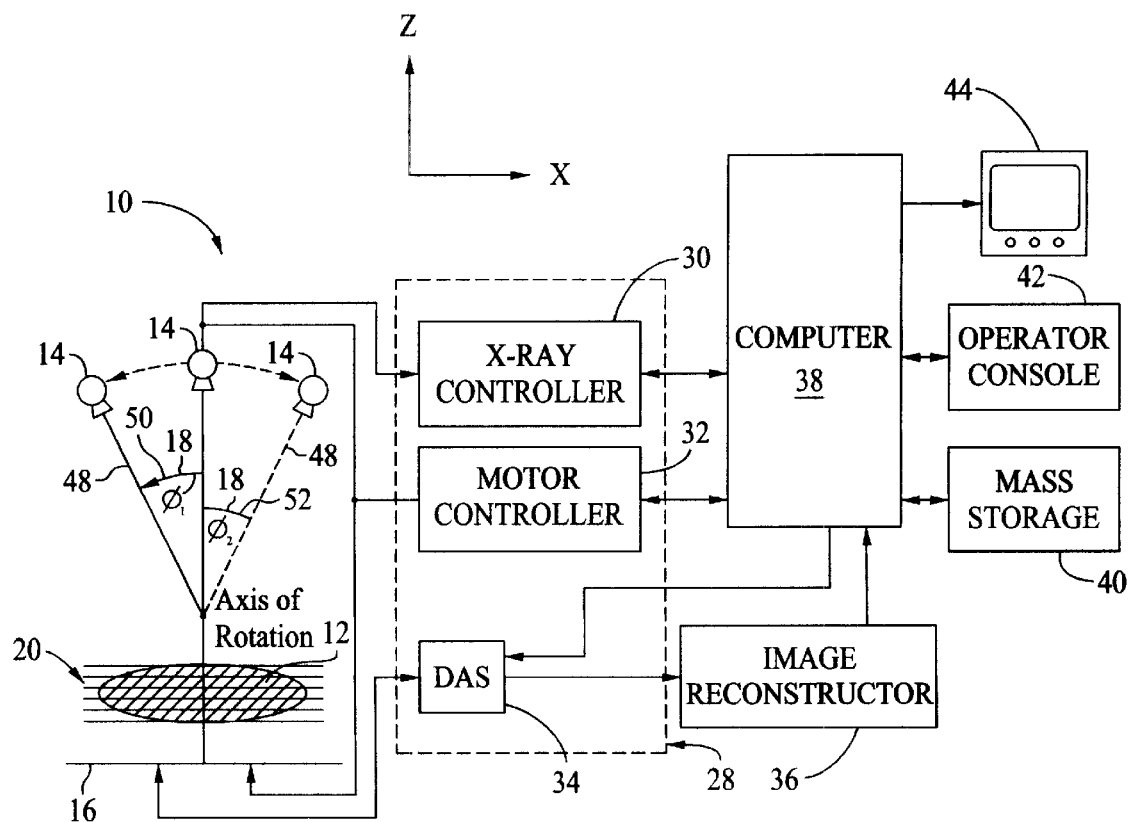
FIG. 1 is a pictorial view of a tomographic imaging system

Referring to FIG. 1 and in an exemplary embodiment, a digital imaging system 10 generates a three-dimensional dataset representative of an imaged object 12, such as a patient's breast 12 in mammographic tomosynthesis. System 10 includes a radiation source 14, such as an x-ray source 14, and at least one detector array 16 for collecting views from a plurality of projection angles 18. Specifically and in one embodiment, system 10 includes a radiation source 14 which projects a cone-shaped beam of x-rays which pass through object 12 and impinge on detector array 16. The views obtained at each angle 18 can be used to reconstruct a plurality of slices, i.e., images representative of structures located in planes 20 parallel to detector 16. Detector array 16 is fabricated in a panel configuration having a plurality of pixels (not shown) arranged in rows and columns so that an image is generated for an entire object of interest such as breast 12. In one embodiment, detector array 16 is a cardiac detector array 16 and object 12 is a heart 12. Each pixel includes a photosensor, such as a photodiode, that is coupled via a switching transistor to two separate address lines, a scan line and a data line. The radiation incident on a scintillator material and the pixel photosensors measure, by way of change in the charge across the diode, the amount of light generated by x-ray interaction with the scintillator. As a result, each pixel produces an electronic signal that represents the intensity, after attenuation by object 12, of an x-ray beam impinging on detector array 16. In one embodiment, detector array 16 is approximately 20 cm by 20 cm and is configured to produce views for an entire object of interest, e.g., breast 12. Alternatively, detector array 16 is variably sized depending on the intended use. Additionally, the individual pixels on detector array 16 can also be any size depending on the intended use.

In one embodiment, the reconstructed three-dimensional dataset is not arranged in slices corresponding to planes that are parallel to detector 16, but in a more general fashion. In another embodiment, the reconstructed dataset consists only of a single two-dimensional image, or one-dimensional function. In yet another embodiment, detector 16 is a shape other than planar.

In one embodiment, radiation source 14 and detector array 16 are moveable relative to object 12 and each other. More specifically, radiation source 14 and detector array 16 are translatable so that the projection angle 18 of the imaged volume is altered. Radiation source 14 and detector array 16 are translatable such that projection angle 18 may be any acute or oblique projection angle.

The operation of radiation source 14 is governed by a control mechanism 28 of imaging system 10. Control mechanism 28 includes a radiation controller 30 that provides power and timing signals to radiation source 14 and a motor controller 32 that controls the respective translation speed and position of radiation source 14 and detector array 16. A data acquisition system (DAS) 34 in control mechanism 28 samples digital data from detector 16 for subsequent processing. An image reconstructor 36 receives sampled and digitized projection dataset from DAS 34 and performs high-speed image reconstruction, as described herein. The reconstructed three-dimensional dataset, representative of imaged object 12, is applied as an input to a computer 38 which stores the three-dimensional dataset in a mass storage device 40. Image reconstructor 36 is programmed to perform functions described herein, and, as used herein, the term image reconstructor refers to computers, processors, microcontrollers, microcomputers, programmable logic controllers, application specific integrated circuits, and other programmable circuits.

Computer 38 also receives commands and scanning parameters from an operator via console 42 that has an input device. A display 44, such as a cathode ray tube and a liquid crystal display (LCD) allows the operator to observe the reconstructed three-dimensional dataset and other data from computer 38. The operator supplied commands and parameters are used by computer 38 to provide control signals and information to DAS 34, motor controller 32, and radiation controller 30.

In use, a patient is positioned so that the object of interest 12 is within the field of view of system 10, i.e., breast 12 is positioned within the imaged volume extending between radiation source 14 and detector array 16. Views of breast 12, are then acquired from at least two projection angles 18 to generate a projection dataset of the volume of interest. The plurality of views represent the tomosynthesis projection dataset. The collected projection dataset is then utilized to generate a three-dimensional dataset, i.e., a plurality of slices for scanned breast 12, representative of the three-dimensional radiographic representation of imaged breast 12. After enabling radiation source 14 so that the radiation beam is emitted at first projection angle 46, a view is collected using detector array 16. Projection angle 18 of system 10 is then altered by translating the position of source 14 so that central axis 48 of the radiation beam is altered to a second projection angle 49 and position of detector array 16 is altered so that breast 12 remains within the field of view of system 10. Radiation source 14 is again enabled and a view is collected for second projection angle 49. The same procedure is then repeated for any number of subsequent projection angles 18.

Figure 2:
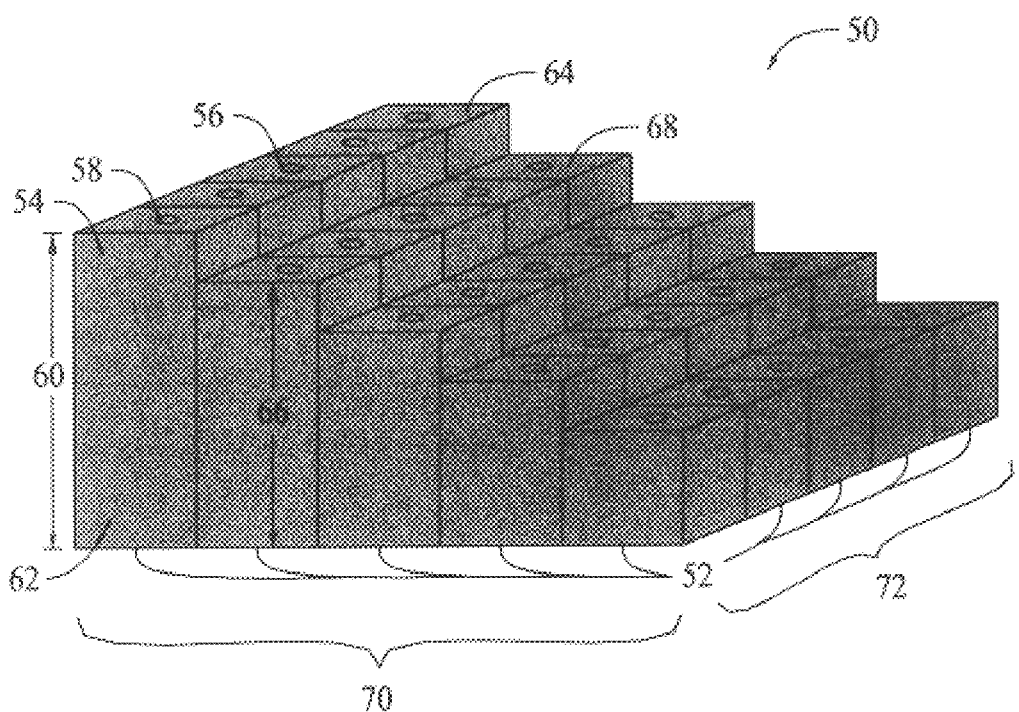
FIG. 2 is a perspective view of an exemplary embodiment of a calibration phantom system.

FIG. 2 is a perspective view of an exemplary embodiment of a calibration phantom system 50 which is non-unitary and includes a plurality of phantom elements 52 including at least a first phantom element material block 54 and at least a second phantom element material block 56 co-positioned on detector 16. First phantom element material block 54 has a first surface 58 at a first height 60, and at least partially includes a first material 62, such as a breast equivalent material 62. First phantom element material block 54 also has a first attenuation coefficient. Second phantom element material block 56 has a second surface 64 at a second height 66 different than the first height 60 an at least partially includes a second material 68, such as a second breast equivalent material 68. Second phantom element material block 56 also has a second attenuation coefficient different than the first attenuation coefficient.

Figure 3:
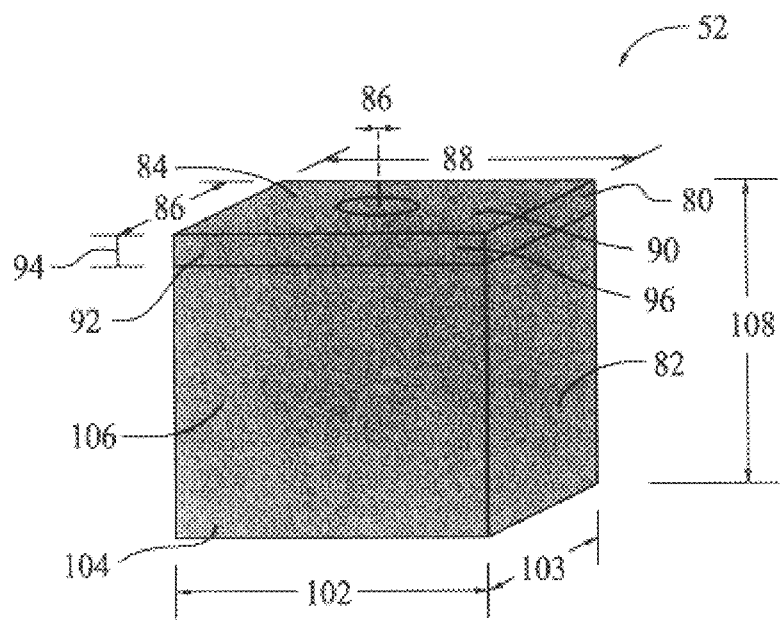
FIG. 3 is a perspective view of an exemplary embodiment of a phantom element of the phantom system illustrated in FIG. 2.

In use, calibration phantom system 50 includes a plurality of phantom elements 52 arranged in a plurality of adjacent rows 70 and adjacent columns 72. In one embodiment, first phantom element material block 54 and second phantom element material block 56 are positioned in decreasing order of attenuation coefficient. In another embodiment, first phantom element material block 54 and second phantom element material block 56 are positioned in decreasing order of height. Alternatively, a plurality of phantom elements 52 arranged in some other configuration can be used because the profile of attenuation coefficients across the calibration phantom system 50 is a design choice and need not correspond to the one shown in FIG. 2. In one embodiment phantom elements 52 are co-positioned on detector 16 such that phantom elements 52 are in the field of view of x-ray source 14. In one embodiment, the least attenuating material corresponds to the tissue equivalent of fat, which is expected to have the least x-ray attenuation in a real human breast. The most attenuating material corresponds to the tissue equivalent of glandular/breast mass tissue, which is expected to have the most x-ray attenuation of normally occurring non-calcified tissue in a human breast. In an alternative embodiment, higher attenuation coefficient materials, such as the tissue-equivalent of calcium phosphate or calcium oxalate may also be used FIG. 3 is a perspective view of an exemplary embodiment of a phantom element 52 shown in FIG. 2 which includes a radiation shielding plate 80 and an element material block 82. Radiation shielding plate 80 facilitates a reduction in radiation beams contacting element material block 82. In an alternative embodiment, phantom element 52 does not include radiation shielding plate 80.

In one embodiment, radiation shielding plate 80 is substantially rectangular. Alternatively, radiation shielding plate 80 is substantially square, oval, or circular. Radiation shielding plate 80 is substantially solid or uniform and includes an opening 84 having a width 86. Radiation shielding plate 80 also includes a length 88, a first surface 90, a second surface 92, and a thickness 94, that is measured between first surface 90 and second surface 92. Width 86, length 88 and thickness 94 are variably selected depending on the intended use of radiation shielding plate 80. In one embodiment, first surface 90 and second surface 92 are substantially parallel and opening 84 extends from first surface 90, through radiation shielding plate 80, to second surface 92. Alternatively, radiation shielding plate 80 is substantially solid or uniform, without intentional openings, internal voids or internal passages. In one embodiment, opening 84 is substantially circular and has a diameter which is between 0.5 mm and 5 mm, although any diameter which is appropriate to the calibration phantom element, the calibration task at hand, and the desired scatter rejection can be used. Alternatively, opening 84 is variably selected depending on the intended use of radiation shielding plate 80. In an alternative embodiment, radiation shielding plate 80 includes a plurality of slits (not shown). In one embodiment, radiation shielding plate 80 includes a metallic material 96, such as, but not limited to, lead, tungsten, and aluminum. Metallic material 96 is selected to facilitate an increase or decrease in x-ray attenuation. In one embodiment, radiation shielding plate 80 substantially covers element material block 82. Alternatively, radiation shielding plate 80 covers a portion of element material block 82. In another embodiment, radiation shielding plate 80 covers none of element material block 82.

Element material block 82 is substantially solid or uniform, without intentional internal voids or internal passages. In one embodiment, element material block 82 is substantially rectangular. In an alternative embodiment, element material block 82 is substantially square, spherical, or a shape having a oval cross-section. Element material block 82 includes a width 100, a length 102, a first surface 104, a second surface 106, and a height 108 that is measured between first surface 104 and second surface 106. Height 108 is variably selected depending on the intended use. In one embodiment, first surface 104 and second surface 106 are substantially parallel. In one embodiment, element material block 82 includes, but is not limited to, a breast equivalent material. Alternatively, element material block 82 includes real tissue (not shown). In one embodiment, radiation shielding plate 80 is frictionally coupled to element material block 82 to facilitate removal of radiation shielding plate 80 during calibration.:

Element material block 82 includes an attenuation spectrum $\mu_i(E)$, i.e. the attenuation coefficient is a function of photon energy E, over its height 108, where E is an x-ray photon energy and $\mu_i$ is an attenuation coefficient of a single x-ray in the spectrum. In one embodiment, width 100 and length 102 are variably selected to facilitate calibration. For example, due to scatter kernel effects, phantom elements 52 with the smallest heights 108 can be machined to be smallest in footprint, i.e. element region on the detector. Alternatively, phantom elements 52 may be non-rectangular, i.e. "pointed" to facilitate pointing the phantom element 52 to a source focal spot, to facilitate changing a specific geometry of phantom element 52. A phantom "warping" (shearing) from the design shown is possible and may be useful for calibration tasks with known geometries.

Figure 4:
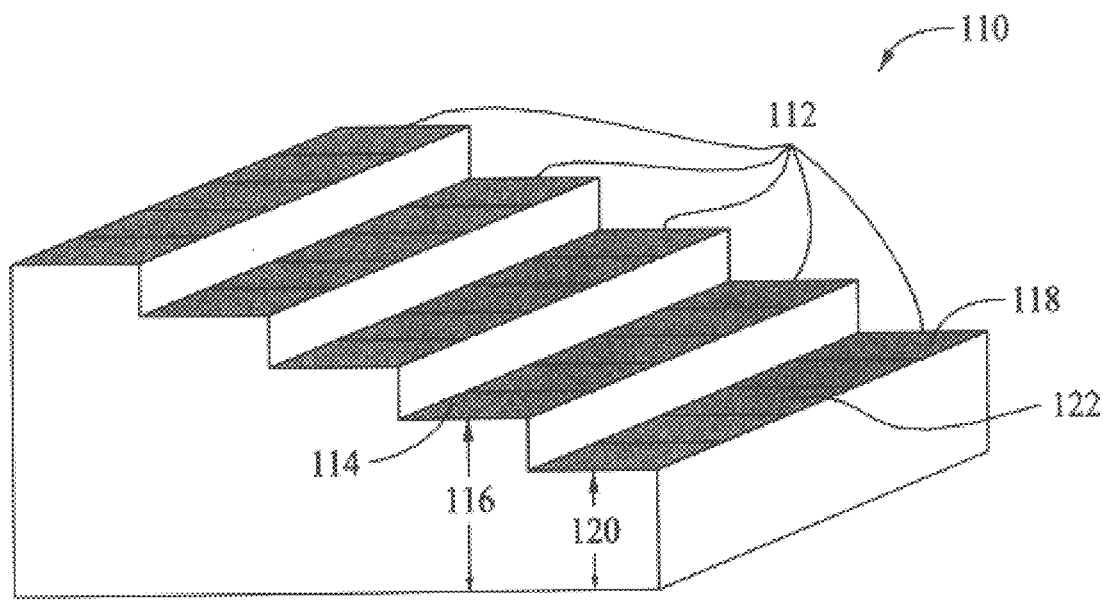
FIG. 4 is a perspective view of another exemplary embodiment of a calibration phantom system.

FIG. 4 is a perspective view of another exemplary embodiment of a calibration phantom system 110. Calibration phantom system 110 is unitary and includes a plurality of phantom projections 112 wherein each phantom projection includes a first surface 114 at a first height 116, a second surface 118 at a second height 120 different than the first height 116. Calibration phantom system 110 is fabricated using a spatially varying gradient of materials 122, such as breast equivalent materials 122. In one embodiment, calibration phantom system 110 is injection-molded, i.e. a mix of constituent polymer concentrations are controlled over the injection so that the material composition varies spatially, although other approaches could yield similar properties in calibration phantoms.

In use, heights 116 and 120 are chosen to approximately match the expected breast thickness variations seen in a medical clinic. For example, the smallest height chosen may be approximately 3 cm. and the largest may be approximately 7 cm. Alternatively, any arbitrary sampling of the height distributions may be used, depending on the purposes of the calibration.

Figure 5:
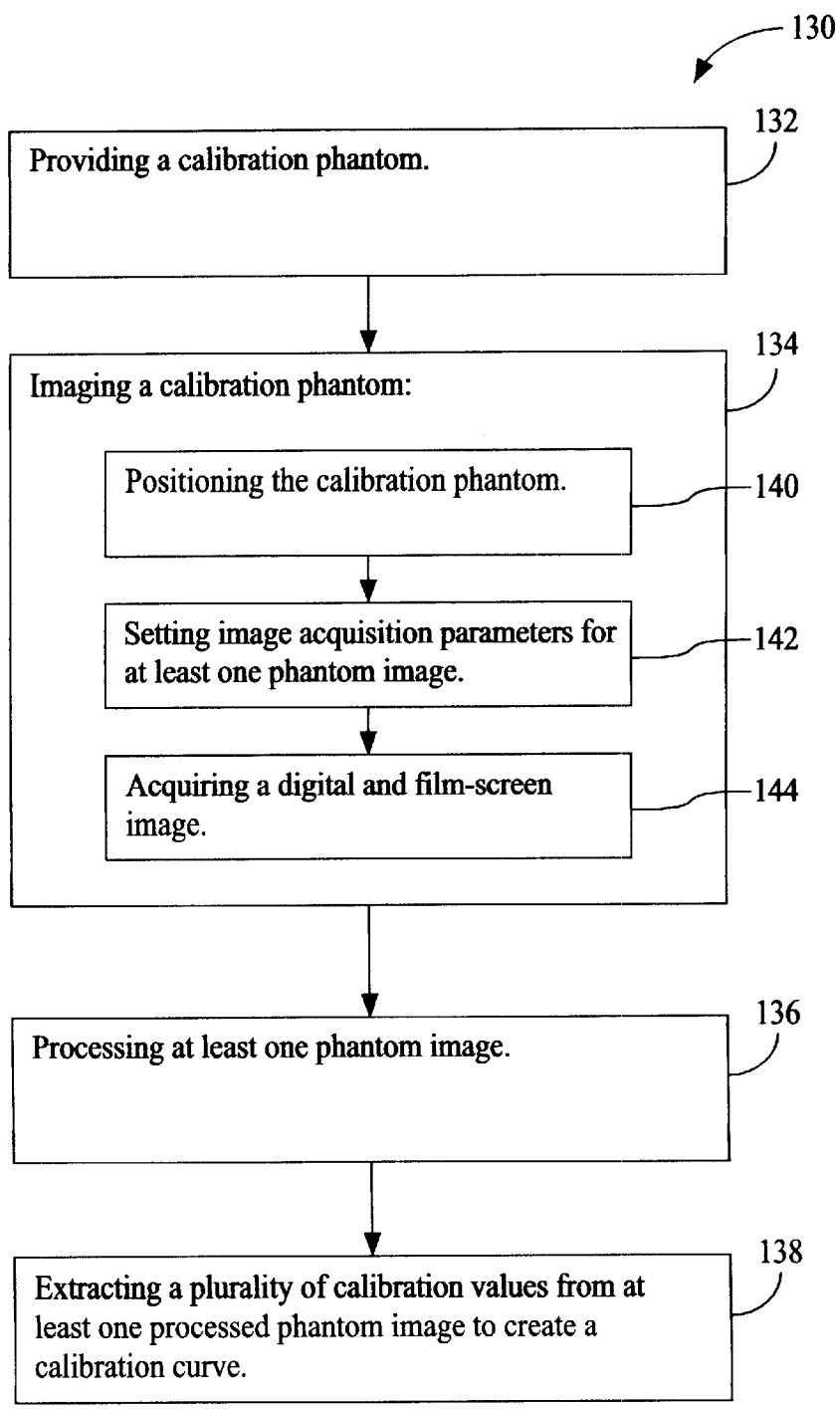
FIG. 5 is a flow diagram of a method including imaging a calibration phantom system.

FIG. 5 is a flow diagram of a method 130 including providing 132 a calibration phantom system, imaging 134 the calibration phantom system with medical imaging system 10 (shown in FIG. 1) to generate at least one phantom image, processing 136 at least one phantom image, and extracting 138 a plurality of calibration values from at least one processed 136 phantom image to create a calibration curve.

Providing 132 a calibration phantom system includes providing a calibration phantom system 50 (shown in FIG. 2) and a calibration phantom system 110 (shown in FIG. 4). Alternatively, a plurality of alternative embodiments of calibration phantom systems 50 can be provided.

Imaging 134 calibration phantom system 50 with medical imaging system 10 (shown in FIG. 1) to generate at least one phantom image includes positioning 140 calibration phantom system 50 between radiation source 14 (shown in FIG. 1) and detector array 16 (shown in FIG. 1), setting 142 image acquisition parameters for at least one phantom image, and acquiring 144 at least one digital image and at least one film-screen image. In one embodiment, positioning 140 calibration phantom system 50 includes, translating, rotating, and tilting calibration phantom system 50, such that calibration phantom system 50 is between radiation source 14 and detector array 16. In one embodiment, calibration phantom system 50 is contacting a known anti-scatter grid (not shown). Alternatively, the anti-scatter grid is not used and calibration phantom system 50 is positioned on detector array 18. In another embodiment, calibration phantom system 50 is suspended at a point between radiation source 14 and detector array 16. In a further embodiment, a compression paddle (not shown) or some other device is used to position calibration phantom system 50 between radiation source 14 and detector array 16. Setting 142 image acquisition parameters dependent upon any particular x-ray technique employed, the parameters include 1) the anode material 2) the filter material 3) the kVp (peak kiloelectronVolt photon energy produced), and mAs, which is a measure of charge. Typical choices for anode materials are: a) Molybdenum, b) Rhodium or c) Tungsten. The filter type could be any material. Typically, the filter is a) Molybdenum or b) Rhodium. However, other choices for the filter material in the mammography energy range include Cu, Al, W, and lucite. The kVp for mammography energies is typically between 15 keV and 49 keV. The mAs is typically between 4 mAs and 250 mAs. One choice for each of those four variables, the filter, the anode, the kVp, and the mAs make up an "acquisition parameter set", which describe one instance of what is called "x-ray technique" in practice. For instance, using Rh/Rh, Mo/Rh or Mo/Mo (3 filter/anode combinations) techniques with kVps between 20 and 40 (21 options) and either 50, 60, 70, 80, 90, or 100 for the mAs (6 values), an operator can choose between potentially 3×21×6=378 different x-ray techniques. At least one technique is required to acquire at least one phantom image. At least one phantom image is acquired after calibration phantom system 50 has been positioned. Acquiring 144 a digital and film-screen image includes acquiring a plurality of images at multiple energies, such as dual energy mammography, and multiple filter and anode combinations. For example, using calibration phantom system 50, a calibration procedure may include acquisition from 20 kilo-electron volts (keV) to 40 keV on a number of different filter/anode combinations. Processing 136 at least one phantom image for each calibration phantom system 50 can be tailored to specific phantom element 52 arrangements and configuration in the image acquisition process described herein. Alternatively calibration phantom system 110 can be used for all imaging methods described herein.

Figure 6:
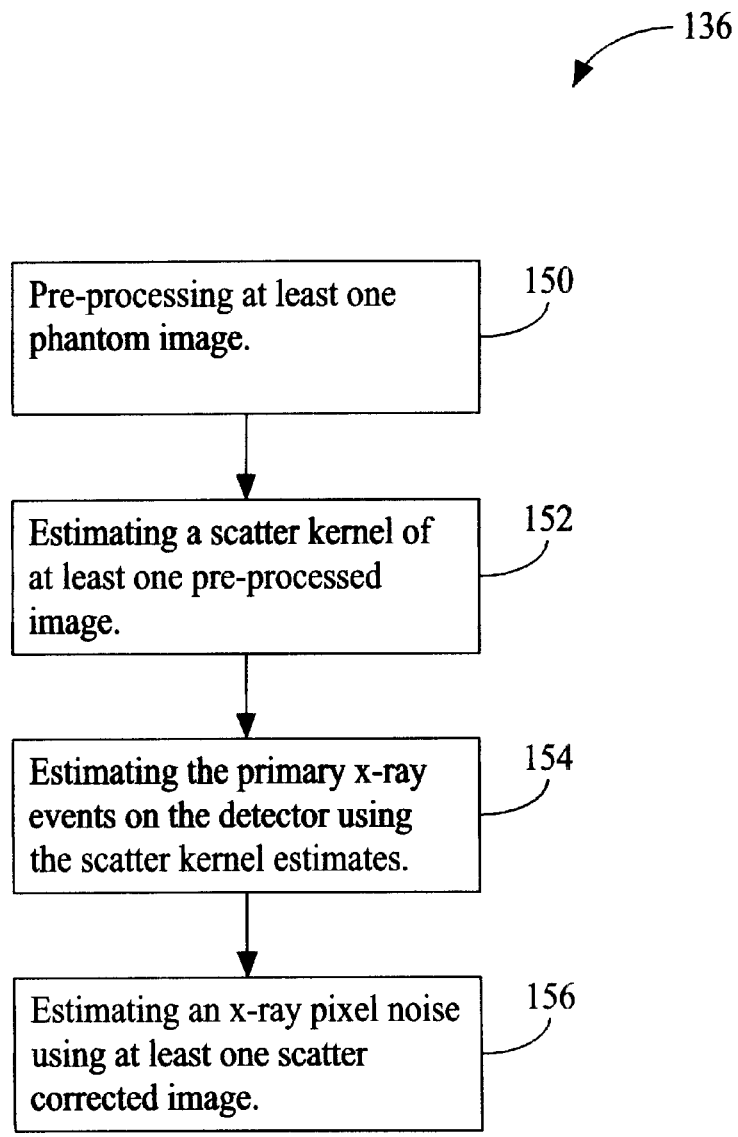
FIG. 6 is a flow diagram of a portion of the method shown in FIG. 5 including preprocessing the phantom element.

FIG. 6 is a flow diagram of a portion of method 130 (shown in FIG. 5) including processing 136 at least one phantom image. Processing 136 at least one phantom image includes pre-processing 150 at least one phantom image, estimating 152 a scatter kernel of at least one pre-processed image, correcting 154 scatter using at least one scatter kernel estimation, and estimating 156 x-ray pixel noise using at least one scatter corrected image.

Pre-processing 150 at least one phantom image may include dark-frame correction, i.e. where an x-ray scan is acquired with no x-ray radiation prior to the phantom image acquisition. The "dark-frame" image may be subtracted from the phantom image. Alternatively, the image can be gain-corrected or independently corrected, i.e. corrected by the operator, for the angle of x-ray incidence effects on detector array 16. Gain correction and independent correction are used to account for a variable flux of radiation source 14 over detector array 16. In use, an effective flux on an individual pixel (not shown) can be calculated using a function related to the cosine of the angle from the anode to the specific digital detector pixel, or in the case of film-screen, to the specific location on the film.

Estimating 152 a scatter kernel using at least one pre-processed image includes using radiation shielding plate 80 (shown in FIG. 3) and a plurality of calibration phantom systems, such as, calibration phantom system 50 and calibration phantom system 110. Alternatively, estimating 152 a scatter kernel using at least one pre-processed image may be accomplished without using radiation shielding plate 80. More specifically, scatter kernel estimations can be adjusted to compensate for the amount of scatter and primary x-ray event reduction in different imaging system arrangements, such as an imaging system including an anti-scatter grid, and an imaging system not including an anti-scatter grid. Further, scatter kernel estimations can be adjusted according to the amount of scatter and primary x-ray event reduction in different phantom element arrangements, such as images acquired directly on detector 16 with the anti-scatter grid removed, and images acquired near radiation source 14. In an exemplary embodiment, estimating 152 a scatter kernel using at least one pre-processed image includes acquiring phantom images with an radiation shielding plate 80 which extends over a surface of element material block 82 and includes opening 86.

In one embodiment, estimating 152 a scatter kernel using at least one pre-processed image also includes locating peaks corresponding to primaries under opening 84, estimating scatter kernel support, i.e. the kernel locations with values greater than some small constant, and using a priori information on phantom elements 52, i.e. material block heights, opening diameter, phantom element 52 arrangement, phantom element 52 configuration, i.e. scatter grid or no scatter grid, suspended above detector 16 or directly on detector 16, and other geometric effects. Estimating 152 a scatter kernel also includes estimating a scatter kernel shape, amplitude, and amplitude of primary x-ray events using a plurality of deconvolution techniques, such as Fourier and spatial domain, on any subset of the phantom element detector footprints. A scattered x-ray event means that a photon emitted at the anode toward detector 16, during the x-ray's trajectory through a material, deflected off of an atomic nucleus in the material block such that the x-ray's trajectory deviates substantially from a straight line. All other x-ray photons which are emitted from the anode and impinge on the detector are referred to as primaries herein.

In another embodiment, estimating 152 a scatter kernel using at least one preprocessed image is made by acquiring a plurality of phantom images using an radiation shielding plate 80 which extends over a portion of element material block 82 and includes an opening 82. Estimating 152 a scatter kernel of at least one preprocessed image also includes estimating the location of scatter or scatter and primary event edges using a priori information based on phantom elements 52 arrangement and configuration, estimating edge spread function using the primary event edge locations, and estimating a scatter kernel using a priori information of the scatter kernel or the physics which define the scatter kernel properties.

In a further embodiment, estimating 152 a scatter kernel using at least one preprocessed image includes acquiring a plurality of phantom images without using an radiation shielding plate 80. Estimating 152 a scatter kernel using at least one preprocessed image also includes estimating edge locations between events which are purely scatter and events which are due to combinations of scattered and primary x-ray photons, estimating edge locations between a plurality of breast equivalent materials 62, 68, and estimating edge locations between a plurality of breast-equivalent material phantom element heights 66, 60. The edge information may be available a priori from a phantom position measurement. Scatter kernel estimation also includes, estimating a scatter kernel support using a plurality of edge locations, estimating a plurality of spatially varying primary and scattered x-ray event contributions using the kernel support estimates, and solving the inverse problem of primary estimation from observations of scattered and primary radiation.

In one embodiment using calibration phantom system 50 including radiation shielding plate 80, estimating 152 scatter kernel using at least one preprocessed image includes determining the pixel locations of the primary x-ray events on calibration phantom system 50, using a combination of spatially-dependent edge detection, thresholding, and morphological operators to generate primary x-ray footprints.

Using the primary x-ray footprints, and the assumption that that the scatter kernel is circularly symmetric, the useful range of $r_T$ (where r is the polar version of the Cartesian coordinates, $r=\sqrt{x^2+y^2}$) for the kernel estimation procedure can be determined. In one embodiment, and referring to FIG. 3, a range of $r_T$ for phantom element 52 will be less than width 100 divided by two or length 102 divided by two. In use, $r_T$ will also be larger than pinhole diameter 86 divided by two (called $r_p$ herein). Alternatively, $r_T$ can be variably selected depending on the specific calibration task.

In one embodiment, the useful range of $r_T$ is determined using r, where the average signal level $y(r,\theta)$ averaged over $\theta$, drops to R % of its average value inside $r=r_p$. In one embodiment, the useful range of r for estimation of scatter kernel parameters is $r<r_p$, and $y(r,\theta)$ is greater than $\beta$ for $r<r_p$. For example, one choice for the useful signal level for scatter kernel estimation can be the radius where the average signal level drops below R=5% of the average signal level of $y(r,\theta)$ inside $r=r_p$.

Further, a parametric model for the scatter kernel is determined using the useful range of $r_T$. In one embodiment, a parametric model for scatter kernel is:

$$K_g(r)=\alpha_1 G(r;o,\sigma_1)=\alpha_2 G(r;o,\sigma_2)+ \ldots \alpha_n G(r;o,\sigma_n) \quad \text{Equation 1}$$

where is the parametric model for the scatter kernel in polar coordinates, $g(x;\mu,\sigma)$ is a two-dimensional circularly symmetric Gaussian in x with mean $\mu$ and standard deviation $\sigma$. In the parametric model describe herein, the observed mean signal is a sum of a constant term inside the $r=r_p$ circle of radially symmetric Gaussians with different amplitudes, $\alpha_k$, and variances, $\sigma_k$, all centered at the origin.

In another embodiment, a parametric model for scatter kernel is:

$$K_e(r) = a_e \exp\left(\frac{-r}{\lambda}\right) \quad \text{Equation 2}$$

where $K_e(r)$ is a parametric model the scatter kernel in polar coordinates, $a_e$ is the amplitude of a radially symmetric decaying exponential with spatial time constant $\lambda$. In one embodiment, $K_e$ and $K_g$, are only two choices for the parametrization of the scatter kernel. In an alternative embodiment, any parametrization that captures the spatially-varying properties of the scatter kernel can be used.

In one embodiment, using a scatter kernel described herein, a model for scatter is:

$$y_c=P+P*K+\eta \quad \text{Equation 3}$$

where $y_c$ is an observed image, P is a deterministic component of a photon count data due to primary, i.e. unscattered, x-rays, P convolved with K is the deterministic but unknown scattered photon count data component and $\eta$ is the noise (quantum noise and electronic noise) in the system. In use, this estimation approach can be used for general scatter kernels, K, and so can be applied to $K_e$ or $K_g$ in Equations 1 and 2 or any other kernel representation. One model for P in polar coordinates is that $P=\beta$ for $r<rp$, and $P=0$ for $r>rp$.

Figure 7:
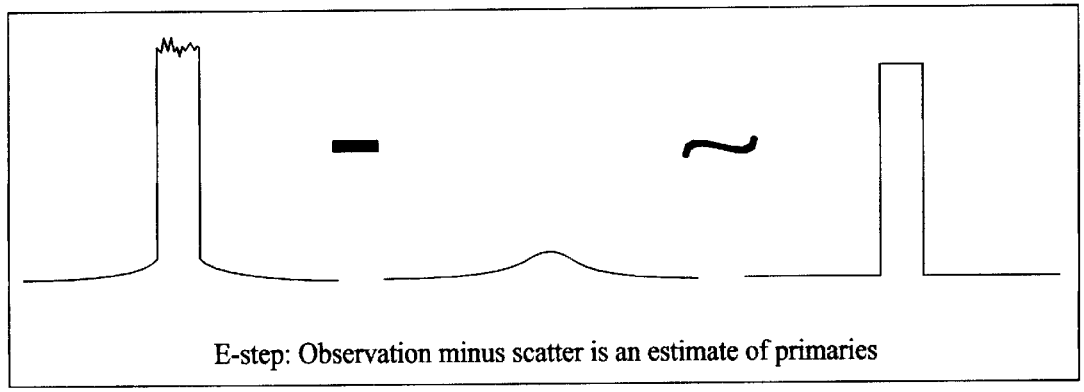
FIG. 7 is a plot illustrating EM scatter kernel parameter estimation.
Figure 7:
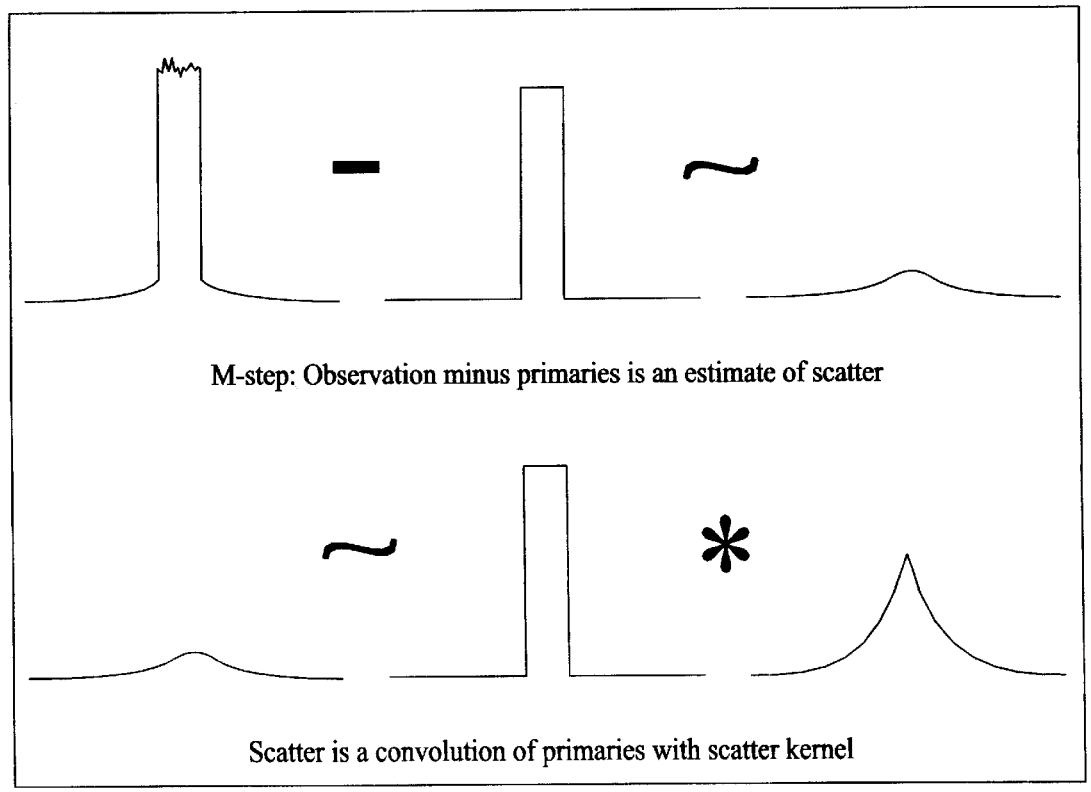

FIG. 7 is plot illustrating EM scatter kernel parameter estimation. In one embodiment, a maximum likelihood (ML) estimation approach to the identification of the scatter kernel parameters is used. In one embodiment, ML estimation of the primary and scattered events is accomplished using an expectation-maximization (EM) algorithm. The EM algorithm requires the definition of an E-step, a M-step, and an initialization.

In one embodiment, the EM algorithm can be determined by computing the expectation (E-step) of the complete data at the iteration, at the $j^{th}$ iteration, $\beta^j=E[\beta|y_c,K^{j-1}]$, wherein $\beta^j$ the estimate of the constant signal level inside $r_p$ which correspond to the primaries from the E-step. $\beta$ is the estimate of the observed signal due only to primaries. For example, setting $K=K_g$ in equation 1, the E-step is $\beta^j=E[\beta|y_c, \alpha_k^j,\sigma_k^j]$, alternatively, setting $K=K_e$ in equation 2, the E-step is $\beta^j=E[\beta|y_c,\alpha_e^{j-1}, \lambda^{j-1}]$. Given $B^j$, maximize the likelihood (M-step) of the scatter kernel parameters given the expected value of scatter: $\alpha_k^j,\sigma_k^j=\arg \max\ p(\alpha_k^{j-1},\sigma_k^{j-1}|y_c,\alpha,\beta)$. In general, the E-step corresponds to estimating the primary x-ray events given the scatter kernel. The M-step corresponds to estimating the scatter kernel properties assuming that the primary events are known. This concept is illustrated in FIG. 7.

A initial estimate of the primary events is determined to initialize the overall EMs. In one embodiment, the initialization is:

$$\beta^0 = \frac{1}{\pi r_p^2} \int_0^{r_p} y_c(r) \cdot r \cdot dr \cdot d\theta \quad \text{Equation 4}$$

where $\beta_0$ corresponds to the average photon counts in an aperture. Alternatively, any initialization which allows convergence to the ML estimate of the scatter kernel can be used.

The EM algorithm can used to update the kernel parameters of the scatter kernel model on the $j^{th}$ iteration of the EM algorithm using a priori information available from the phantom element parameters. A priori information includes information such as if the pinhole cover hole is a circle of radius d mm, then $r_p=5d$, assuming a point source located directly above the center of the pinhole, and pixel pitch=100 microns. For alternate pixel pitch sizes, the same analysis can be applied, where 2p pixels, where d and p are the pinhole diameter and pixel pitch in mm. For rays where the pinhole center-point source line is not perpendicular to the detector, an appropriate geometric transformation can be applied to the primary and scattered x-ray footprint. In use, the transformation warps the observed footprint in detector space to the footprint expected in detector space for a point source located directly above the pinhole center.

In one embodiment, depending on a desired fidelity, to a first approximation, the geometric transformation can also be omitted, and $\beta^j$ can be estimated using:

$$\beta^0 = \frac{1}{\pi r_p^2} \int_0^{r_p} y_c(r) - \beta^{j-1} p_{r_p}(r) * K(r) r \cdot dr \cdot d\theta$$

where $p_a(r)$ is a rectangular pulse of width $\alpha$ from r=0 to $r=\alpha$, and K is the scatter kernel, $K_e$, $K_g$ or any other scatter kernel estimate from the $j^{th}$ iteration can be used for K. For example, if $K(r)=K_g(r;\alpha_i,\sigma_i)$, $a_i$ and $\sigma_i$ are estimates of the amplitudes and standard deviations of the Gaussian components of the scatter kernel estimated at the previous iteration of the EM algorithm. Alternatively, if $K(r)=K_e(r)$, $a_e$ and $\lambda$ are the amplitude and lambda estimates from the previous iteration.

The M-step requires a definition of the incomplete data, g, "completed" by the estimate of the primary radiation through the aperture which is computed in the parameter estimate from the E-step. The M-step is:

$$g^j = y_c(r) - \beta^{j-1} p_{r_p}(r) \quad \text{Equation 6}$$

As illustrated, the incomplete data is an observation minus an expectation of a primary radiation component in an aperture at a previous iteration. A ML approach to the estimation of scatter kernel parameters is then used. This can be approached in a transform space, such as Fourier or wavelet space, or can be approached in the spatial domain, itself. In one embodiment, an approach is to first generate an estimate of the scatter kernel using a regularized Fourier analysis. For example, if $G(\omega)$ is a spatial frequency representation of $g^j(r)$, and $\Phi(\omega)$ is a spatial frequency estimate of the primary radiation through an aperture, P, a theoretical scatter kernel frequency domain representation is:

$$\tilde{K}(r) = \tau^{-1}\left[\frac{G(\omega)}{\Phi(\omega)}\right] \quad \text{Equation 7}$$

where $\tau^{-1}$ indicates the inverse Fourier transform. In use, scatter kernel estimation is complicated by zeros in the frequency domain representation, $\Phi(\omega)$, of the primary radiation. Known regularization approaches can be applied to ameliorate this difficulty. In one embodiment, one approach is to set a floor for the Fourier coefficients of $\Phi(\omega)$. When the Fourier coefficients in $\Phi(\omega)$ fall below the floor, the corresponding coefficient in the ratio is set to zero. In this way, the estimate of K(r) is made insensitive to the specific form of $\Phi(\omega)$. Given the estimate of K(r), a plurality of parameter fitting routines can be applied to the kernel parameters, i.e. if K is indeed parameterized, as it is for $K_e$ and $K_g$. Alternatively, the regularized estimate of K(r) for the next iteration can be used. For example, a plurality of ML Gaussian mixture fitting routines can be applied to estimate the parameters for the scatter kernel in equation 1, such as an EM approach to the parameter estimation in the M-step. The EM approach described is therefore a nested EM approach.

In one embodiment, an approach can be refined with additional constraints. For example, constraining $a_k > 0$ and constraining scatter kernel means to be zero refines the parameter search space to kernels of interest. In this way, we can estimate the set of $a_k$ and $\sigma_k$. Alternative approaches to the M-step include relaxed Fourier analysis, energy minimization approaches, and iterated conditional expectation approaches. Alternatively, any approach which yields an ML estimate of kernel parameters can be used. The EM scatter kernel parameter estimation procedure is shown diagrammatically in FIG. 7.

Estimating 154 the primary x-ray events on the detector using the scatter kernel estimates include using the scatter kernel estimation determined previously herein and the prior information on the phantom element arrangement. The primary events can be estimated in a plurality of methods. In one embodiment, if scatter estimation is not necessary, and since the collimation of apertures in the radiation shielding plate shields significantly reduces the scatter contribution inside the aperture, the primary estimate can approximated by the mean count data inside the x-ray aperture footprint or the detector. Alternatively, if the scatter contribution is known, but scatter kernel estimation P not specifically required, some fraction of the mean count data inside the x-ray aperture can be used to estimate the primary radiation contribution. Alternatively, any embodiment of the E-step from the EM approach to estimation of primaries in the scatter kernel estimation can be used. In some embodiments, the scatter can be neglected, and it need be neither estimated or subtracted from the measured counts.

Estimating 156 x-ray pixel noise using at least one scatter corrected image includes estimating the noise contributions from the primary and scattered radiation contributions to calculate the noise on the primaries given the estimates of primary and scattered radiation contributions. Alternatively, the expected noise in the scatter kernel region can be determined by modeling using a Poisson distribution of x-ray events rather than estimate those noise parameters from the imagery directly. Another alternative to noise estimation is to remove radiation shielding plate 80 and acquire another x-ray image and estimate noise using that image. An alternative to noise estimation is to model the noise as a function of material block composition and use these estimates for computing error bars on tissue composition estimates. In use, when estimating noise from the images themselves or as theoretical values based on material block composition, a plurality of metrics can be used to quantify the variability including standard deviation, variance, robust statistics, and Hausdorff metrics on subregions of photon counts.

In one embodiment, the noise variance is used. Using a subregion of a specified image, and using known calibration phantom geometry, i.e., x-ray aperture footprint, the noise can be estimated using a simple model of the scatter and primary noise contributions. For example, using cover plate 80 the photon count noise can be estimated using Equation 8.

$$\sigma_p^2 = \frac{1}{\pi r_T^2} \int_o^{r_T} \int_{\theta=0}^{\theta=2\pi} \frac{([y(r,\theta) - (E(y(r,\theta)))])^2}{E(y(r,\theta))} \cdot r \cdot dr \cdot d\theta \quad \text{Equation 8}$$

wherein the variable $r_T$ is used to describe the useful radius for noise power estimation.

Extracting 138 a plurality of calibration values from at least one processed phantom image to create a calibration curve includes using the primary events and noise estimations to create a calibration curve. In use, the primary x-ray events (photon counts) at the detector due to each phantom element are calculated. The attenuation coefficient for the $i^{th}$ material block can be estimated using the following relationship:

$$\bar{\mu}_i = \frac{d\log(\beta_i(T))}{dT} \quad \text{Equation 9}$$

where $\beta_i(T)$ is the photon count data as a function of thickness for a specific material block composition. For example, the attenuation coefficients for both fat and glandular can be estimated using Equation 9. In use, the function may be fit with a polynomial, spline, or other curve useful for calculation of the derivative in equation 9 because the continuous version of $\beta(T)$ may not be known, or known only at a selected number of thicknesses, T.

While the invention has been described in terms of various specific embodiments, those skilled in the art will recognize that the invention can be practiced with modification within the spirit and scope of the claims.

What is claimed is:

1. A calibration phantom system for use with an imaging system, said calibration phantom comprising:
   a first phantom element material block having a first surface at a first height, said first phantom element material block at least partially comprising a first material having a first attenuation coefficient;

a second phantom element material block having a second surface at a second height different than said first height, said second phantom element material block at least partially comprising a second material having a second attenuation coefficient different than said first attenuation coefficient, said first phantom element material block and said second phantom element material block co-positioned on a detector;

a first radiation shielding plate positioned on top of said first phantom element material block, said first radiation shield plate having at least one opening extending therethrough; and a second radiation shielding plate positioned on top of said second phantom element material block, said second radiation shield plate having at least one opening extending therethrough.

2. A calibration phantom element material block in accordance with claim 1 wherein said first phantom element material block is substantially rectangular.

3. A calibration phantom system in accordance with claim 1 wherein said first radiation shielding plate is substantially rectangular.

4. A calibration phantom system in accordance with claim 1 wherein said element material block comprise a breast-equivalent material.

5. A calibration phantom system in accordance with claim 1 wherein said first phantom element and said second phantom elements are co-positioned in decreasing order of attenuation coefficients.

6. A calibration phantom system in accordance with claim 1 wherein said radiation shielding plate extends over a surface of said element material block.

7. A calibration phantom system in accordance with claim 1 wherein said radiation shielding plate comprises a metallic material.

8. A calibration phantom system in accordance with claim 7 wherein said radiation shielding plate at least partially comprises at least one of lead, tungsten, and aluminum.

9. A method for calibration of an imaging system, the imaging system including a radiation source and a digital detector, said method comprising:

providing a calibration phantom system including a first phantom element material block having a first surface at a first height, said first phantom element material block at least partially comprising a first material having a first attenuation coefficient, and a second phantom element material block having a second surface at a second height different than said first height, said second phantom element material block at least partially comprising a second material having a second attenuation coefficient different than said first attenuation coefficient, said first phantom element material block and said second phantom element material block co-positioned on a detector;

imaging the calibration phantom system to obtain phantom images using the digital detector and radiation source;

processing the phantom images;

extracting a plurality of calibration values from the processed phantom images; and using the calibration values to adjust a plurality of pixel intensities in the acquired images.

10. A method in accordance with claim 9 wherein imaging the calibration phantom system comprises:

positioning the calibration phantom system on the digital detector;

setting image acquisition parameters for at least one image; and acquiring at least one digital image and at least one film-screen image.

11. A method in accordance with claim 9 wherein processing the phantom images comprises:

pre-processing at least one phantom image;

estimating a scatter kernel of at least one pre-processed image;

estimating the primary x-ray events on the detector using the scatter kernel estimates; and estimating a radiation pixel noise using the primary x-ray events.

12. A method in accordance with claim 11 wherein estimating a scatter kernel comprises estimating a scatter kernel using a radiation shielding plate having at least one opening extending therethrough.

13. A method in accordance with claim 12 wherein using a radiation shielding plate comprises using a radiation shielding plate which extends over a surface of an element material block.

14. A method in accordance with claim 9 wherein extracting a plurality of calibration values from the processed phantom images comprises extracting calibration values from the processed image to calculate a calibration curve.

15. A method for calibration of an imaging system, the imaging system including a radiation source and a digital detector, said method comprising:

providing a calibration phantom system including a first phantom element material block having a first surface at a first height, said first phantom element material block at least partially comprising a first material having a first attenuation coefficient, and a second phantom element material block having a second surface at a second height different than said first height, said second phantom element material block at least partially comprising a second material having a second attenuation coefficient different than said first attenuation coefficient, said first phantom element material block and said second phantom element material block co-positioned on a detector;

imaging the calibration phantom system to obtain phantom images, wherein said imaging comprises positioning the calibration phantom system on the digital detector;

setting image acquisition parameters for at least one image, and acquiring at least one digital image and at least one film-screen image;

processing the phantom images, wherein said processing comprises pre-processing at least one phantom image, estimating a scatter kernel of at least one pre-processed image, estimating the primary x-ray events on the detector using the scatter kernel estimates, and estimating a radiation pixel noise using the primary x-ray events; and extracting a plurality of calibration values from the processed phantom images.

16. A computer readable medium encoded with a program executable by a computer for calibration of an imaging system, the imaging system including a radiation source and a digital detector, said program configured to instruct the computer to:

image the calibration phantom system to obtain phantom images, wherein the calibration phantom system includes a first phantom element material block having a first surface at a first height, said first phantom element material block at least partially comprising a first material having a first attenuation coefficient, and a second phantom element material block having a second surface at a second height different than said first height, said second phantom element material block at least partially comprising a second material having a second attenuation coefficient different than said first attenuation coefficient, said first phantom element material block and said second phantom element material block co-positioned on a detector, a first radiation shielding plate positioned on top of said first phantom element material block, said first radiation shield plate having at least one opening extending therethrough; and a second radiation shielding plate positioned on top of said second phantom element material block, said second radiation shield plate having at least one opening extending therethrough;

process the phantom images;

extract a plurality of calibration values from the processed phantom images.

17. A computer readable medium in accordance with claim 16 wherein to image the calibration phantom system, said program further configured to:

position the calibration phantom system on the digital detector;

set image acquisition parameters for at least one image; and acquire at least one digital image and at least one film-screen image.

18. A computer readable medium in accordance with claim 16 wherein to process the phantom images, said program further configured to:

pre-process at least one phantom image;

estimate a scatter kernel of at least one pre-processed image;

estimate the primary x-ray events on the detector using the scatter kernel estimates; and estimate a radiation pixel noise using the primary x-ray events.

19. A computer readable medium in accordance with claim 18 wherein to estimate a scatter kernel, said program further configured to estimate a scatter kernel using a radiation shielding plate.

20. A computer readable medium in accordance with claim 16 wherein to extract a plurality of calibration values from the processed phantom images, said program further configured to extract calibration values from the processed image to calculate a calibration curve.

21. A computer readable medium in accordance with claim 18 wherein to estimate a scatter kernel, said program further configured to estimate a scatter kernel using a radiation shielding plate extending over a surface of an element material block.

22. A computer readable medium encoded with a program executable by a computer for calibration of an imaging system, the imaging system including a radiation source and a digital detector, said program configured to instruct the computer to:

provide a calibration phantom system including a first phantom element material block having a first surface at a first height, said first phantom element material block at least partially comprising a first material having a first attenuation coefficient, and a second phantom element material block having a second surface at a second height different than said first height, said second phantom element material block at least partially comprising a second material having a second attenuation coefficient different than said first attenuation coefficient, said first phantom element material block and said second phantom element material block co-positioned on a detector;

image the calibration phantom system to obtain phantom images, wherein said imaging comprises positioning the calibration phantom system on the digital detector;

setting image acquisition parameters for at least one image, and acquiring at least one digital image and at least one film-screen image;

process the phantom images, wherein said processing comprises pre-processing at least one phantom image, estimating a scatter kernel of at least one pre-processsed image, estimating the primary x-ray events on the detector using the scatter kernel estimates, and estimating a radiation pixel noise using the primary x-ray events; and extract a plurality of calibration values from processed phantom images.

23. A computer readable medium in accordance with claim 20 wherein to estimate a scatter kernel, said program further configured to estimate a scatter kernel using a radiation shielding plate extending over a surface of an element material block.

* * * * *